US005260260A

United States Patent [19]
Gednalske et al.

[11] Patent Number: 5,260,260
[45] Date of Patent: Nov. 9, 1993

[54] NONIONIC HERBICIDAL AND SURFACTANT BLEND

[75] Inventors: Joe V. Gednalske, Apple Valley; Robert W. Herzfeld, Stillwater, both of Minn.

[73] Assignee: Cenex/Land O'Lakes Agronomy Company, St. Paul, Minn.

[21] Appl. No.: 881,473

[22] Filed: May 11, 1992

[51] Int. Cl.[5] ............... A01N 57/12; A01N 47/36; A01N 37/34
[52] U.S. Cl. ............... 504/206; 504/214; 504/215; 504/234; 504/253; 504/310; 504/116; 71/DIG. 1
[58] Field of Search ............... 71/113, DIG. 1, 86, 71/92, 105; 504/116, 206, 214, 215, 234, 253, 310

[56] References Cited

U.S. PATENT DOCUMENTS 4,463,547 3/1984 Sampson .................. 71/76
4,557,751 12/1985 Ronning et al. .......... 71/91

OTHER PUBLICATIONS

McCutcheons Emulsifiers and Detergents, 1990, McCutcheon Publishing Co, p. 192.
The Agrochemicals Handbook, 3rd Ed, Kidd et al (editor), Royal Society of Chemistry, 1991.
The Merck Index, 10th Ed, Windholz et al (editor), Merch & Co, 1983, p. 1249.
Van Valkenburg, "Adjuvants for Herbicides", pp. i–ii, 1–8, 1979.
Puritch, *Pesticidal Soaps and Adjuvants—What are They and How do They Work?*, 23rd Annual Lower Mainland Horticultural Improvement Association Growers' Short Course, Feb. 11–13, 1981, pp. 53–66.

*Primary Examiner*—Allen J. Robinson
*Assistant Examiner*—B. Bembenick
*Attorney, Agent, or Firm*—Kinney & Lange

[57] ABSTRACT

A nonionic surfactant blend for use with compatible herbicides. The nonionic surfactant blend includes an effective amount of an acidulated soybean soapstock. The acidulated soybean soapstock includes a range of total fatty acids of about 94%-to-96% by volume and a moisture content of not more than about 5% by volume. The present invention also includes a method for improving the performance of a herbicide. The method includes providing an effective quantity of the improved nonionic surfactant blend for combination with the herbicide.

1 Claim, No Drawings

NONIONIC HERBICIDAL AND SURFACTANT BLEND

BACKGROUND OF THE INVENTION

The present invention relates to a nonionic surfactant blend having an acidulated soybean soapstock component, for use with a compatable herbicide. The present invention also relates to a method of making the nonionic surfactant blend.

Liquid herbicides and dry, flowable herbicides are mixed with water in order to more economically apply the herbicides to crops. However, liquid and dry herbicides, even when mixed in water, have a limited capacity to pass through a leaf surface and then to translocate within a weed. A surfactant is added to the liquid and dry, flowable herbicides in order to help the herbicides enter the leaf surface of the weed. Once the herbicide enters a leaf surface of a weed, the herbicide can be translocated to an action site within the weed and can kill the weed.

Surfactants are also used to disperse herbicides in water. The surfactants include a lipophilic portion compatible with many herbicides and a hydrophilic portion compatible with water. Depending upon the herbicide, the surfactant used is suitably either ionic or nonionic.

Ionic surfactants include a molecular structure having a charge on the hydrophilic portion of the structure. Ionic surfactants having a positive charge are cationic surfactants. Ionic surfactants having a negative charge are anionic surfactants.

Nonionic surfactants include a molecular structure where the nature of chemical bonds within the structure impart hydrophilic and lipophilic features to the surfactant. Nonionic surfactants do not have a net charge. Nonionic surfactants are usually products of a petrochemical process. Consequently, the nonionic surfactants tend to be expensive and to have limited environmental compatibility.

Surfactants interact with herbicides in a number of ways both before and after application to a crop. In addition to having use as an emulsifier, a surfactant may act as a penetrant, spreader, sticker, stabilizer, wetting agent, dispersant and defoamer. The surfactant may affect a rate of drying of a droplet on a plant and the nature of a residue, liquid or crystal. The surfactant may influence the weathering characteristics of the herbicide, including rewetting characteristics.

SUMMARY OF THE INVENTION

The present invention includes a method for making a nonionic surfactant blend having an acidulated soybean soapstock component, the nonionic surfactant blend, and a method for combining the blend with a compatible herbicide to make an improved herbicidal mixture. The method for making the blend includes providing an effective amount of an acidulated soybean soapstock for addition to a nonionic surfactant, nonoxynol. The acidulated soybean soapstock and nonionic surfactant are then mixed to make the nonionic surfactant blend. The nonionic surfactant blend includes the nonionic surfactant, nonoxynol, and an effective amount of the acidulated soybean soapstock. The method for combining the nonionic surfactant blend with a herbicide includes providing an effective quantity of the nonionic surfactant blend for combination with a compatible herbicide to form the improved herbicidal mixture.

DETAILED DESCRIPTION OF THE PREFERRED EMBODIMENTS

The present invention includes a method for making a nonionic surfactant blend, the nonionic surfactant blend and a method of combining the blend with a compatible herbicide to form an improved herbicidal mixture. The method for making the nonionic surfactant blend includes providing an effective concentration of acidulated soybean soapstock in a particular mixing order and combining the acidulated soybean soapstock with a nonionic surfactant to make the nonionic surfactant blend. The nonionic surfactant blend includes the components of the acidulated soybean soapstock and a nonionic surfactant, nonoxynol. The blend preferably also includes a viscosity reducing agent, water, and antifoam. The method for using the nonionic surfactant blend includes combining a compatible herbicide with the nonionic surfactant blend at an effective concentration to make an improved herbicidal mixture.

The method for making the surfactant blend of the present invention includes providing and mixing components in a particular order to make a nonionic surfactant blend that is homogeneous. The method for making the nonionic surfactant blend of the present invention includes providing the ingredient of nonoxynol in an effective concentration range. Preferably, the effective concentration ranges from about 38% to 80% by volume of the nonionic surfactant blend. The effective concentration range is determined by the performance of the concentration in promoting translocation of a compatible herbicide in a weed and by cost of the concentration. Most preferably, the concentration is about 59.5% by volume.

The method also includes providing the acidulated soybean soapstock in an effective quantity. The effective quantity ranges from about 10% to 30% by volume. Most preferably, the effective quantity is about 20% by volume of the nonionic surfactant blend. The effective quantity is determined by the performance of the quantity to promote translocation of a compatible herbicide in a weed and by solubility of the acidulated soybean soapstock in the nonionic surfactant blend.

The method also includes providing a viscosity reducing agent in an effective quantity. Preferred viscosity reducing agents include isopropanol and n-butanol. The effective quantity ranges from about 5% to 10% by volume of the nonionic surfactant blend for either isopropanol or n-butanol. Most preferably, the concentration is about 10% by volume. The effective concentration reduces viscosity of the nonionic surfactant blend to a viscosity that promotes ease of handling of the nonionic surfactant blend. The method also includes providing water in an effective quantity that preferably ranges from about 5% to 10% by volume of the nonionic surfactant blend. The effective quantity of water reduces cost of using the blend without reducing performance of the blend.

Preferably, the method for making the nonionic surfactant blend also includes providing an antifoam such as Dow Corning A Antifoam manufactured by Dow Chemical of Midland, Michigan, that is about 0.5% by volume. The method may also optionally include providing a fatty acid ethoxylate of up to 20% by volume. Preferred concentration ranges for components provided and mixed to make the nonionic surfactant blend are described in Tables 1 and 2.

Most preferably, the nonionic surfactant blend is made by adding an effective quantity of nonoxynol to water. Then an effective quantity of viscosity reducing agent is added to the nonoxynol-water dispersion. In a next step, the acidulated soybean soapstock is added and mixed with the nonoxynol-viscosity reducing agent dispersion. Then, antifoam such as Dow Corning A Antifoam TM (Midland, Michigan) is added to the dispersion. The mixing order illustrated in Table 1 is the most preferred in the manufacture of the nonionic surfactant blend. Once mixed, the nonionic surfactant blend may be stored at any ambient temperature without changing consistency or activity.

TABLE 1

| % By Vol. | Ingredients | Mixing Order |
|---|---|---|
| 59.5 | Nonoxynol | 1 |
| 20.0 | Acidulated Soybean Soapstock | 4 |
| 10.0 | Viscosity Reducing Agent | 3 |
| 10.0 | Water | 2 |
| 0.5 | Dow Corning a Antifoam | 5 |

In another embodiment, the nonionic surfactant, nonoxynol, additionally includes a fatty alcohol ethoxylate. The mixing order for the nonionic surfactant including the fatty alcohol ethoxylate is described in Table 2.

TABLE 2

| % By Vol. | Ingredients | Mixing Order |
|---|---|---|
| 10-20 | Fatty Alcohol Ethoxylate | 2 |
| 38.6-49.5 | Nonoxynol | 1 |
| 10-30 | Acid. Soybean Soapstock | 5 |
| 5-10 | Viscosity Reducing Agent | 4 |
| 5-10 | Water | 3 |
| 0.2-0.5 | Anti-foam | 6 |

The acidulated soybean soapstock component that is provided and mixed to make the nonionic surfactant blend is a brown liquid and has a specific gravity of about 0.95. The acidulated soybean soapstock is highly viscous. In order to reduce the viscosity, the acidulated soybean soapstock is heated to a minimum temperature of about 72° F. prior to mixing with other ingredients of the nonionic surfactant blend.

Even when heated, the high viscosity of the acidulated soybean soapstock limits the effective quantity of acidulated soapstock to not more than 30% by volume of the total nonionic surfactant blend volume. The high viscosity of the acidulated soybean soapstock may cause handling problems if the concentration by volume exceeds 30%. Most preferably, the concentration of the acidulated soapstock does not exceed about 20% by volume of the nonionic surfactant blend.

The acidulated soybean soapstock used in the blend of the present invention is formed by the complete acidulation of soybean soapstock. Soybean soapstock is a byproduct of the alkali refining of soybean oil. In soybean oil processing, crude soybean oil is treated with dilute sodium hydroxide. In other acceptable embodiments, the crude soybean oil is treated with soda ash or a combination of sodium hydroxide and soda ash. The sodium hydroxide and soda ash react with free fatty acids in the crude soybean oil fraction to neutralize the free fatty acids and to form a soapstock. The soapstock is typically separated from the oil by centrifugation or settling. The soapstock is then treated with sulfuric acid in an acidulation step.

Soybean soapstock is about 6% of the total volume of crude soybean oil refined. The free fatty acids in acidulated soybean soapstock are typically less than one percent of the total volume of crude soybean oil refined. Soybean soapstock is also called "foots" since the soapstock accumulates in the bottom of a refining tank. Acidulated soybean soapstock is regarded as a relatively unrefined waste product of soybean oil processing, having only limited commercial use by soap manufacturers and animal feed producers.

A contract grade of acidulated soybean soapstock preferably includes not less than 85% total fatty acids by volume. Most preferably, the acidulated soybean soapstock used in the blend of the present invention includes a total fatty acid concentration range of about 94%-to-96% by volume as shown in Table 3. The acidulated soybean soapstock also includes a moisture concentration of not more than about 5% by volume. One typical analysis of acidulated soybean soapstock for use in the present invention, manufactured by the Honeymead Products Company of Mankato, Minnesota, is described in Table 3. One typical analysis of a fatty acid profile for acidulated soybean soapstock for use in the present invention is shown in Table 4.

TABLE 3

| Acid Value | 80-130 |
|---|---|
| Total Fatty Acids | 94%-96% |
| Color | Dark |
| Iodine Value | 118-130 |
| Moisture (Karl-Fischer) | 5% max |

TABLE 4

| FATTY ACID PROFILE | % OF TOTAL FATTY ACIDS |
|---|---|
| 14:0 myristic acid | 0.1 |
| 16:0 palmitic acid | 14.1 |
| 18:0 stearic acid | 4.8 |
| 18:1 oleic acid | 21.0 |
| 18:2 linoleic acid | 52.2 |
| 18:3 linolenic acid | 6.9 |
| 20:0 arachidic acid | 0.3 |
| 22:0 behenic acid | 0.4 |

All testing was performed by approved American Oil Chemists Society methods.

The nonoxynol component of the nonionic surfactant blend is described in U.S. Pat. No. 2,313,477. The nonoxynol is also known by chemical names that include α-(nonylphenyl) -ω-hydroxypoly(oxy-1,2-ethanediyl); polyethyleneglycol ether; mono(nonylphenyl)ether; macrogol nonylphenyl ether; polyoxyethylene(n)-nonylphenyl ether; nonylphenyl polyethyleneglycol ether; nonylphenoxypolyethoxyethanol; and poly(oxy-1,2 ethanediyl)-α-(nonphyenol)-Ω-hydroxy, CAS Registry No. 00009016-45-9. The nonoxynol has a chemical formula,

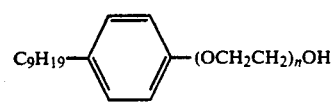

The "n" of the chemical formula preferably ranges from 8 to 10 carbon atoms. The "n" is most preferably 9 carbon atoms. The nonoxynol provided to the blend of the present invention preferably includes about 100% nonoxynol by volume. However, the nonoxynol added may acceptably include a fatty acid ethoxylate in a concentration of up to 20% by volume to form a nonoxynol-ethoxylate solution.

The nonionic surfactant blend includes ingredients of nonoxynol, acidulated soybean soapstock, a viscosity reducing agent such as isopropanol or n-butanol, and water in effective concentration ranges. Effective ranges include about 38% to 80% by volume for nonoxynol, about 10% to 30% for acidulated soybean soapstock, about 5% to 10% for viscosity reducing agent, and about 5% to 10% for water. The nonionic surfactant blend also acceptably includes fatty alcohol ethoxylate and antifoam in effective concentration ranges. The ranges include about 10% to 20% by volume for adding fatty alcohol ethoxylate and about 0.2% to 0.5% by volume for antifoam.

The acidulated soybean soapstock is provided and mixed with the nonionic surfactant blend to replace a portion of the nonoxynol used in an application such as a herbicide dispersion. A benefit of replacing a portion of nonoxynol with acidulated soybean soapstock is a reduced cost of using the nonionic surfactant blend. Another advantage of replacing a portion of nonoxynol for acidulated soybean soapstock is an improved environmental compatibility. Acidulated soybean soapstock, unlike nonoxynol, is utilized as an animal food and is biodegradable.

The nonionic surfactant blend is combined with a compatible herbicide to form an improved herbicidal mixture. The herbicide concentration of the mixture is applied to a field at a concentration that acceptably ranges from about 0.004 lb/acre to about 2 lb/acre. The preferred concentration depends upon the herbicide combined to make the mixture. The herbicidal mixture is acceptably supplemented with nitrogen. Nitrogen is acceptably added as urea ammonium nitrate (UAN) in a preferred concentration of up to about 28% by weight as nitrogen. The nonionic surfactant blend of the present invention is acceptably added to the improved herbicidal mixture at a concentration within the range of about 0.125% to 1% by volume. The remaining volume of the improved herbicidal mixture is comprised of water. The improved herbicidal mixture is preferably applied to the soil as a spray. However, any conventional method of application is suitable for use in the present invention.

The nonionic surfactant blend of the present invention is compatible with a wide variety of compatible herbicides that include nicosulfuron DF manufactured by DuPont (Wilmington, DE)--2(((((4,6-Dimethoxypyrimidin-2-yl)aminocarbonyl)-)aminosulfonyl))-N,N-dimethyl-3-pyridinecarboxamide; primisulfuron made by Ciba-Geigy having chemical name 3-[4,6-Bis-(difluoromethoxy)- pyrimidin-2-yl) - 1- (2-methoxycarbonylphenylsulfonyl) urea; clethodim; fluazifop having chemical name (2- [4 [[5- (trifluoromethyl) - 2-pyridinyl]oxy]phenoxy]propanoic acid); quizalofop; sethoxydim having chemical name (2-[1-(ethoxyimino)butyl]-5-[2-(ethylthio)propyl]-3-hydroxy-2-cyclohexen-1-one); imazethapyr having chemical name 2-[4,5-dihydro-4-methyl-4-(1-methylethyl)-5-oxo-1H-imidazole-2-yl]-3-pyridinecarboxylic acid; fomesafen; acifluorfen having chemical name (5-[2-chloro-4-(trifluoromethyl)-phenoxy]-2-nitrobenzoic acid); laptofen; bentazon having chemical name 3-isopropyl-1H -2,1,3-ben zothiadiazin-4-(3H)-1,2,2-d ioxide; trifensulfuron having chemical name methyl 3-[[[[(4-methoxy-6-methyl- 1 , 3 , 5-triazin - 2-yl) amino]carbonyl]amino]sulfonyl]-2-thiophenecarboxylate; chlorimuron made by (DuPont) having chemical name 2-[[[[4-chloro-6-methoxypyrimidin-2-yl)amino]-carbonyl]amino]sulfomyl]benzoate; imazaquine; paraquat having chemical name (1,1'-dimethyl-4,4'-bipyridinium); glyphosate having chemical name (N-(phosphonomethyl)glycine) (Monsanto); tribenuron; chlorsulfuron having chemical name (3-(2-chloro-9H-thioxanthen-9-ylidene)-N, N-dimethyl-1-propanamine) and metsulfuron.

The nonionic surfactant blend component of the herbicidal mixture maintains an adequate reduction in surface tension for good herbicide coverage and also aids in herbicide uptake. Examples 1 through 10 include tests in which the nonionic surfactant blend of the present invention significantly improved herbicide performance when compared to a first nonionic surfactant. The composition of the nonionic surfactant blend employed in examples 1-10 is described in Table 1.

The first surfactant blend included a nonionic surfactant that was about 60% by volume, alcohol that was about 10% by volume, water that was about 10% by volume and refined, purified fatty acids that were about 20% by volume. That the nonionic surfactant blend having the relatively unrefined acidulated soybean soapstock component improved herbicide efficacy in many instances when compared to a blend having refined purified fatty acids is unexpected.

The method of the present invention of combining the nonionic surfactant blend with a compatible herbicide to form a herbicidal mixture improves performance of the herbicide. The improved performance is measurable as reducing cost of application while maintaining and in some instances, increasing efficacy of the herbicide as is shown in Examples 1-10.

The examples presented are intended to illustrate the performance of the improved nonionic surfactant blend and not to limit the methods and blend of the present invention.

EXAMPLE 1

Woolly Cupgrass Control in Corn

The efficacy of the herbicide nicosulfuron, 2( ( ( ( ( 4,6- Dimethoxypyrimidin - 2-yl) aminocarbonyl)-)aminosulfonyl))-N,N-dimethyl-3-pyridinecarboxamide, manufactured by DuPont Co. (Wilmington, DE) was tested when used in 4 different herbicidal mixtures in killing Woolly Cupgrass in corn. Two of the mixtures included surfactant blends. A first surfactant blend, denoted "Surf" in Table 5, included a nonionic surfactant (about 60% by volume), alcohol (about 10% by volume), water (about 10% by volume), and purified fatty acids (about 20% by volume). The "Surf" blend included about 90% by volume active material.

A second surfactant blend was the improved surfactant blend of the present invention. The improved surfactant blend was denoted "Inv" in Table 5. The composition of the improved surfactant blend is described in Table 1.

A third mixture denoted "Surf+28% N", included the first surfactant blend, "Surf" and Nitrogen. Nitrogen concentration was about 28% by weight as urea ammonium nitrate (UAN). Nitrogen concentration was about 4% by volume as nitrogen of the improved herbicidal mixture.

A fourth herbicidal mixture denoted "COC" in Table 5, included a Crop Oil Concentrate in a concentration of 1% by volume. Crop Oil Concentrate is a petroleum based additive having about 17% emulsifiers. Crop Oil Concentrate is generally considered to convey to herbicides a greater penetrability than nonionic surfactants.

Each of the herbicidal mixtures was applied to a respective test plot of corn having Woolly Cupgrass that was 12 to 18 inches tall. The herbicidal mixtures were applied at a rate of 0.047 lbs per acre as nicosulfuron. The surfactant concentration was 0.25% by volume for surfactants of herbicidal mixtures tested.

The data on Woolly Cupgrass control was collected according to a Randomized Complete Block (RCB) design. The data was analyzed by calculating the least significant difference (LSD) for a confidence interval ($\alpha$) of 0.05.

The least significant difference for a confidence interval of 0.05 was a percent control of 12%. Thus, the herbicidal mixture of nicosulfuron and the surfactant blend of the present invention controlling 90% of Woolly Cupgrass performed significantly better than the mixture of nicosulfuron and first surfactant blend controlling 76% of Woolly Cupgrass as shown in Table 5. The herbicidal mixtures of nicosulfuron and Crop Oil Concentrate and nicosulfuron and the first surfactant and nitrogen each had a percent control within the least significant difference of 12% control. Thus, these mixtures were not significantly different from the herbicidal mixture of the present invention. However, this result demonstrates that the improved herbicidal mixture performed as well as a COC that is regarded as performing better than a nonionic surfactant.

TABLE 5

Woolly Cupgrass Control in Corn

| Treatment | LB/Acre | % Surf. by Vol. | % N. by Vol. | Final Evaluation % Control |
|---|---|---|---|---|
| Nicosulfuron + Surf | .047 | .25 | | 76 |
| Nicosulfuron + surf + 28% N | .047 | .25 | 4 | 79 |
| Nicosulfuron + INV | .047 | .25 | | 90 |
| Nicosulfuron + COC | .047 | 1 | | 78 |

EXAMPLE 2

Wild Prosso Millet Control in Corn

The efficacy of nicosulfuron (DuPont, Wilmington, DE) in killing Wild Prosso Millet in a corn crop when combined to form one of four herbicidal mixtures was tested. The nicosulfuron mixtures were each applied at a concentration of 0.03 lbs per acre as nicosulfuron. The first surfactant and surfactant blend of the present invention were each applied at a concentration of 0.25% by volume of the respective herbicidal mixture. The first surfactant, described for Example 1, included the nonionic surfactant that was 60% by volume, alcohol that was 10% by volume, water that was 10% by volume, and refined fatty acids that were 20% by volume. The herbicidal mixtures tested included the blends of Example 1 along with methylated seed oil (MSO), methyl isothiocyanate, as illustrated in Table 6. MSO is a more costly herbicidal additive than a nonionic surfactant. MSO and COC were each applied at a concentration of about 0.25% by volume of the herbicidal mixtures.

The Wild Prosso Millet was about 0.5 to 3 inches tall when fields were exposed to herbicidal mixtures. Data was collected according to a Randomized Complete Block (RCB). Data was analyzed by calculating the least significant difference for a confidence interval ($\alpha$) of 0.05. The least significant difference for a confidence interval of 0.05 was a percent control of 10%. As shown in Table 6, the percent control of Wild Prosso for the mixture of nicosulfuron and the surfactant blend of the present invention was 84%. This control was significantly better than the control achieved with the mixture of nicosulfuron and the first surfactant. The control with the improved herbicidal mixture of the present invention was not significantly better than the combination of nicosulfuron and either MSO or COC.

TABLE 6

Wild Prosso Millet Control in Corn

| Treatment | LB/Acre | % Surf. by Vol. | Final Evaluation % Control |
|---|---|---|---|
| Nicosulfuron + Surf | .031 | .25 | 70 |
| Nicosulfuron + COC | .031 | 1 | 74 |
| Nicosulfuron + MSO | .031 | 1 | 88 |
| Nicosulfuron + INV | .031 | .25 | 84 |

EXAMPLE 3

Woolly Cupgrass Control in Corn

The improved surfactant of the present invention designated "Inv" in Table 7 was applied in a herbicidal mixture with the herbicide cyanazine, (2-[[4-chloro-6-(ethylamino)-1,3,5-triazin-2-yl]amino]-2-methyl-propanenitrile), to a field of corn having 1-to-3 leaf Woolly Cupgrass. The first surfactant (Surf) was applied with cyanazine at the same time on another plot within the corn field. The first surfactant included a nonionic surfactant, (about 60% by volume), alcohol (about 10% by volume), water (about 20% by volume) and purified fatty acids (about 10% by volume). The first surfactant included about 90% by volume active material.

The cyanazine-herbicidal mixtures were applied at a rate of 2 lbs per acre as cyanazine as illustrated in Table 7. The surfactant blend of the present invention was applied at a concentration of 0.25% by volume of total mixture volume applied. The first surfactant was applied at a concentration of 0.25% by volume of the total volume applied.

The test of Woolly Cupgrass control was of Randomized Complete Block design. Data was analyzed by calculating the least significant difference between treatments.

The least significant difference for a confidence interval of 0.05 was a percent control of 25%. As shown in Table 7, the difference between percent control of cyanazine and the blend of the present invention of 75% was more than 25% higher than the cyanazine and first surfactant percent control of 48%. Thus, the mixture including the nonionic surfactant blend of the present invention performed significantly better than the herbicidal mixture including the first surfactant.

TABLE 7

Woolly Cupgrass Control in Corn

| Treatment | LB/Acre | % Surf. by Vol. | Final Evaluation % Control |
|---|---|---|---|
| Cyanazine + INV | 2.0 | .25 | 75 |
| Cyanazine + Surf | 2.0 | .25 | 48 |

EXAMPLE 4

Wild Prosso Millet Control in Corn

The improved surfactant blend of the present invention was tested as a herbicidal mixture with cyanazine in one test and with nicosulfuron (DuPont) in another test to control Wild Prosso Millet in corn. The performance of the blend of the present invention was compared to the performance of the first nonionic surfactant at the concentrations indicated in Table 8. The first nonionic surfactant included a nonionic surfactant (about 60% by volume), alcohol (about 10% by volume), water (about 10% by volume) and purified fatty acids (about 20% by volume). The first surfactant included about 90% by volume active material.

All mixtures were applied to respective plots of a corn field at the Southern Experiment Station in Waseca, Minnesota. The herbicidal mixtures were applied to 1–2 leaf Wild Prosso and to 3–5 leaf Wild Prosso, respectively. The data on Wild Prosso Millet control was collected according to a Randomized Complete Block design. Data were analyzed by determining the least significant difference based upon a confidence level of 0.05 between treatments.

For the test of 1–2 leaf stage control, with cyanazine and surfactant blend mixtures applied at a rate of 2.0 lbs per acre as cyanazine, the percent control of the mixture including the surfactant blend of the present invention was much higher than the percent control of the first surfactant mixture—85% versus 48%. The results are shown in Table 8. The least significant difference was 28 percentage points control. Thus, the percent control of the herbicidal mixture with the blend of the present invention was significantly higher than the percent control of the herbicidal mixture having the first surfactant.

The test of 3–5 leaf stage control using a nicosulfuron and surfactant mixture showed the best control at an application of 0.03 lbs per acre as nicosulfuron of the herbicidal mixture.

The least significant difference at a confidence interval of 0.05 was 28% control. Thus, as shown in Table 8, the herbicidal mixture including the surfactant blend of the present invention performed significantly better than the herbicidal mixture having the first surfactant blend—97% control versus 62% control.

A concentration of 0.062 lbs per acre showed control of 91% for the nicosulfuron mixture including the blend of the present invention as shown in Table 8. The first surfactant mixture showed 85% control for the 0.062 lbs per acre. The difference between percent control for the mixture having the blend of the present invention and the first surfactant, applied at 0.062 lbs per acre is not significantly different based on the least significant difference of 28% control.

TABLE 8

| Treatment | LB/Acre | % Surf by Vol. | Final Evaluation % Control |
|---|---|---|---|
| Wild Prosso Millet Control in Corn | | | |
| Cyanazine + Surf | 2.0 | .25 | 48 |
| Cyanazine + INV | 2.0 | .25 | 85 |
| Wild Prosso 3-5 Leaf Stage | | | |
| Nicosulfuron + Surf | .031 | .25 | 62 |
| Nicosulfuron + INV | .031 | .25 | 97 |
| Nicosulfuron + Surf | .062 | .25 | 85 |
| Nicosulfuron + INV | .062 | .25 | 91 |

EXAMPLE 5

Green Foxtail and Red Root Pigweed

Applications of mixtures of bromoxynil, 3,5-dibromo-4-hydroxybenzonitrile, and primsulfuron, 3-[4,6-Bis-(difluoromethoxy)-pyrimidin-2-yl)-1-(2-methoxycarbonyl-phenylsulfonyl) urea, both manufactured by Ciba-Geigy (Basel, Switzerland) and the improved surfactant blend and the first surfactant respectively were made to corn field plots having green foxtail and red root pigweed. The foxtail and red root pigweed were uniformly distributed. The foxtail was 1 to 4 inches in height at the time of application. The pigweed was of 0.5 to 1.5 inches in height. The bromoxynil was applied at 0.25 lbs per acre. The primsulfuron was applied at 0.0178 lbs per acre as described in Table 9. The surfactant concentrations for all mixtures were 0.25% by volume.

The percent control for the herbicidal mixture having the surfactant blend of the present invention was 100% for both foxtail and pigweed. The percent control for the herbicidal mixture combined with the first surfactant blend was 91.25% for foxtail and 85.00% for pigweed. The least significant difference for a confidence interval of 0.05 was 3.76 for the final evaluation as shown in Table 9. The data was collected according to a Randomized Complete Block design. Data was analyzed by a Duncan's Multiple Range Test (MRT).

Mixtures of bromoxynil and nicosulfuron were also tested for control of green foxtail and red root pigweed using data collection and analysis formats described above. Bromoxynil was applied to the corn field at a concentration of 0.25 lbs per acre. The nicosulfuron was applied at a concentration of 0.0469 lbs per acre. The surfactant blends were added at a concentration of 0.125% by volume for each herbicidal mixture.

The mixture including the surfactant blend of the present invention controlled 100% of the foxtail and pigweed as shown in Table 9. The combination including the first surfactant controlled 98.75% of the foxtail and 85.5% of the pigweed. The least significant difference for a confidence interval of 0.05 was 13.95% control. Thus, the performance of the two herbicidal mixtures were not significantly different.

TABLE 9

Green Foxtail and Red Root Pigweed Control in Corn

| Treatment | LB/Acre | % Surf. By Vol. | % Foxtail Control | % Pigweed Control |
|---|---|---|---|---|
| Bromoxynil + Primsulfuron + INV | 0.25 + .0178 | .25 | 100 | 100 |
| Bromoxynil + Primsulfuron + Surf | 0.25 + .0178 | .25 | 91.25 | 85.0 |
| Bromoxynil + | 0.25 + .0469 | .125 | 100 | 100 |

TABLE 9-continued

Green Foxtail and Red Root Pigweed Control in Corn

| Treatment | LB/Acre | % Surf. By Vol. | % Foxtail Control | % Pigweed Control |
|---|---|---|---|---|
| Nicosulfuron + INV Bromoxynil + Nicosulfuron + Surf | 0.25 + .0469 | .125 | 98.75 | 85.5 |

EXAMPLE 6

Foxtail Control in Corn

The surfactant blend of the present invention and the first surfactant blend were tested in mixtures with nicosulfuron (DuPont, Wilmington, DE) for control of 4-leaf foxtail control in corn. The concentration of the nicosulfuron herbicidal mixture applied to the corn field plot was 0.047 lbs per acre for both mixtures as shown in Table 10. Both surfactant blends were added at a concentration of 0.25% by volume of the herbicidal mixture. The herbicidal mixture having the surfactant blend of the present invention controlled 89% of the 4-leaf foxtail while the mixture having the conventional surfactant blend controlled 84% as illustrated in Table 10. The least significant difference for a 0.05% confidence level was 4% control. Thus, the herbicidal mixture including the blend of the present invention performed significantly better than the mixture having the first surfactant.

TABLE 10

Foxtail Control in Corn

| Treatment | LB/Acre | % Surf. By Vol. | Final Evaluation % Foxtail Control |
|---|---|---|---|
| Nicosulfuron + INV | .047 | .25 | 89 |
| Nicosulfuron + Surf | .047 | .25 | 84 |

EXAMPLE 7

Woolly Cupgrass & Volunteer Corn Control in Soybeans

Imazethapyr, 2-[4,5-dihydro-4-methyl-4-(1-methylethy 1) -5-oxo-1H- imidazole-2-yl]-3-pyridinecarboxylic acid, when mixed with several formulations including the surfactant blend of the present invention to form herbicidal mixtures, was tested for control of Woolly Cupgrass and volunteer corn in a soybean field. Applications were made when the Woolly Cupgrass 4–6 inches tall and volunteer corn was 6–10 inches tall. The imazethapyr mixtures were applied at a concentration of 0.063 lbs per acre as imazethapyr as shown in Table 11. The surfactant blend of the present invention and the first surfactant were each applied at a concentration 0.25% by volume of the mixture. Nitrogen was added to each mixture at 1.25% by volume as Nitrogen. The Methylated Seed Oil (MSO) concentration was 1.25% by volume and the Crop Oil Concentrate (COC) concentration was 1.25% by volume.

The mixture including imazethapyr, the surfactant blend of the present invention and nitrogen controlled 83% of the Woolly Cupgrass and 81% of the volunteer corn. The mixtures including the first surfactant blend and nitrogen controlled 79% of the Woolly Cupgrass and 62% of the volunteer corn as shown in Table 11. The least significant difference for a confidence interval of 0.05 was 15% control for Woolly Cup and 23% control for volunteer corn. Thus, the percent control of both Woolly Cupgrass and volunteer corn was not significantly different.

TABLE 11

| | | | Final Evaluation | |
|---|---|---|---|---|
| Treatment | LB/Acre | % Surf. by Vol. | Woolly Cup Control | Volunteer Corn Control |
| Imazethapyr + Surf + 28% N | .063 | 0.25 | 79 | 62 |
| Imazethapyr + MSO + 28% N | 0.63 | 0.94 | 77 | 66 |
| Imazethapyr + COC + 28% N | .063 | 1.25 | 52 | 52 |
| Imazethapyr + INV + 28% N | .063 | 0.25 | 83 | 81 |

EXAMPLE 8

Tumble Mustard Control

Mixtures of the herbicide, glyphosate (Monsanto), having a chemical name N-(phosphoromethyl)-glycine, and the surfactant blend of the present invention and the first surfactant respectively, were tested for Tumble Mustard control. The glyphosate was applied at 0.38 lbs per acre as shown in Table 12. The surfactant blends were 0.50% by volume of the herbicidal mixtures. The mixture including the surfactant blend of the present invention controlled 64.5% of the Tumble Mustard while the mixture having the first surfactant blend controlled 10% as shown in Table 12. The least significant difference for a confidence interval of 0.05 was 33.8% control indicating that the difference between the blend of the present invention and first surfactant was significant. Testing was performed according to Randomized Complete Block design and data was analyzed according to a Duncan's Multiple Range Test (MRT).

TABLE 12

Tumble Mustard Control

| Treatment | LB/Acre | % Surf. by Vol. | Final Evaluation % Control |
|---|---|---|---|
| Glyphosate + Surf | .38 | .50 | 10 |
| Glyphosate + INV | .38 | .50 | 64.5 |

EXAMPLE 9

Lambsquarters Control

The herbicide, Imazethapyr, 2-[4,5-dihydro-4-methyl-4-(1-methylethyl)-5-oxo-1H-imidazole-2-yl]-3-pyridinecarboxylic acid, mixed with nitrogen and the surfactant blend of the present invention and the first surfactant, respectively, was tested for control of Lambsquarters. The imazethapyr was applied at 0.063 lbs per acre as shown in Table 13. The nitrogen was applied at 1 quart UAN for each herbicidal mixture. The surfactants tested were applied at 0.25% by volume of each herbicidal mixture. Testing was performed according to a Randomized Complete Block design. Data was analyzed according to a Duncan's Multiple Range Test (MRT). The imazethapyr mixture including the surfactant blend of the present invention controlled 72.5% of the Lambsquarters as shown in Table 14. The imazethapyr mixture including a first surfactant controlled 60% of Lambsquarters as shown in Table 13. The least significant difference at a confidence interval of 0.05 was 6.5% control. Thus, the difference in control between the first surfactant and the surfactant blend of the present invention was significant.

TABLE 13

Lambsquarters Control

| Treatment | LB/Acre | % Surf. by Vol. | Final Evaluation % Control |
|---|---|---|---|
| Imazethapyr + Surf + 1 qt. UAN | .063 | .25 | 60 |
| Imazethapyr + INV 1 qt. UAN | .063 | .25 | 72.5 |

EXAMPLE 10

Lambsquarters Control

A test was made of Lambsquarters control by combinations of trifensulfuron, methyl 3-[[[[(4-methoxy-6-methyl-1,3,5-triazin-2-yl)amino]carbonyl]amino]sulfonyl]-2-thiophenecarboxylate, nitrogen and either the surfactant blend of the present invention or the first surfactant. Trifensulfuron was added at a concentration of 0.004 lbs per acre as shown in Table 14.

The herbicidal mixtures tested for Lambsquarters control also included of methylchlorimuron, methyl 2-[[[[4-chloro-6-methoxypyrimidin-2-yl)amino]-carbonyl]amino]sulfonyl]benzoate. Methylchlorimuron was added at a concentration of 0.004 lbs per acre as shown in Table 14. One quart of nitrogen as urea ammonium nitrate (UAN) was added to each herbicidal mixture. Surfactant blends were each added at a concentration of 0.125% by volume in a first test and a concentration of 0.25% by volume in a second test. Tests were performed according to a Randomized Complete Block design. Data was analyzed according to Duncan's Multiple Range Test. The best control of 80.0% was obtained with the herbicidal mixture having the improved surfactant blend at the concentration of 0.25%. The least significant difference for a confidence interval of 0.05 was 6.1% control for all of the tests included in Table 14. The percent control was significantly better for the herbicidal mixtures including the surfactant blend of the present invention then the formulation having the first surfactant for all concentrations tested.

TABLE 14

Lambsquarters Control

| Treatment | LB/Acre | Final Evaluation % Control |
|---|---|---|
| Trifensulfuron-Methy + Chlorimuron + .125% Surf + 1 qt. UAN | .004 + .004 | 63.8 |
| Trifensulfuron-Methy + Chlorimuron + .25% Surf + 1 qt. UAN | .004 + .004 | 72.5 |
| Trifensulfuron-Methy + Chlorimuron + .125% INV + 1 qt. UAN | .004 + .004 | 77.5 |
| Trifensulfuron-Methy + Chlorimuron + .25% INV + 1 qt. UAN | .004 + .004 | 80.0 |

The surfactant blend of the present invention was also laboratory and field tested with the 22 most commonly used post emergence herbicides used for wheat control in corn, soybeans and wheat production in the United States. The 22 herbicides include nicosulfuron DF, cyanazine DF, primisulfuron, clethodim, fluazifop, quizalofop, sethoxydim, imazethapyr, fomesafen, acifluorfen, lactofen, acifluorfen & bentazon, bentazon, thifensulfuron, chlorimuron, imazaquin, paraquat, diquat, glyphosate, tribenuron, trifensulfuron & tribenuron and chlorsulfuron & metsulfuron. All products tested showed no signs of incompatibility when mixed with the surfactant blend and water.

Although the present invention has been described with reference to preferred embodiments, workers skilled in the art will recognize that changes may be made in form and detail without departing from the spirit and scope of the invention.

What is claimed is:

1. An improved herbicidal mixture comprising an effective quantity of a compatible herbicide selected from the group consisting of nicosulfuron, cyanazine, bromoxynol, primsulfuron, imazethapyr, glyphosate, trifensulfuron, methyl-chlorimuron, and combinations of these herbicides and an effective quantity of a nonionic surfactant blend, the nonionic surfactant blend comprising an effective quantity of nonoxynol and an effective quantity of acidulated soybeam soapstock.

* * * * *

UNITED STATES PATENT AND TRADEMARK OFFICE
CERTIFICATE OF CORRECTION

PATENT NO. : 5,260,260
DATED : November 9, 1993
INVENTOR(S) : Joe V. Gednalske et al It is certified that error appears in the above-indentified patent and that said Letters Patent is hereby corrected as shown below:

Title Page:

In line 3 of the Abstract, after "soapstock", insert --and an effective quantity of nonoxynol--

Col. 5, line 67, delete "ben zothiadiazin", insert --benzothiadiazin--

Col. 5, line 67, delete "d ioxide", insert --dioxide--

Col. 7, line 52, delete "0.03 lbs", insert --0.031 lbs--

Col. 9, line 51, delete "0.03 lbs", insert --0.031 lbs--

Col. 12, line 8, underneath the heading "TABLE II", insert the heading --Woolly Cupgrass & Volunteer Corn Control in Soybeans--

Col. 12, line 9, after "Final Evaluation", insert --%--

Signed and Sealed this

Twenty-eighth Day of June, 1994

Attest:

BRUCE LEHMAN

*Attesting Officer*  *Commissioner of Patents and Trademarks*